United States Patent [19]

Ghiselli

[11] Patent Number: 5,390,529
[45] Date of Patent: Feb. 21, 1995

[54] METHOD FOR DETERMINING HEAVY HYDROCARBONS IN ROCK MATRICES AND THE APPARATUS FOR THE PURPOSE

[75] Inventor: Claudio Ghiselli, Casalpusterlengo, Italy

[73] Assignee: AGIP S.p.A., Milan, Italy

[21] Appl. No.: 213,707

[22] Filed: Mar. 16, 1994

[30] Foreign Application Priority Data

Mar. 19, 1993 [IT] Italy ............... MI93A000519

[51] Int. Cl.⁶ .................. B09B 3/00; B01N 25/00; B01D 53/04
[52] U.S. Cl. .................... 73/23.41; 95/167; 95/143; 95/93; 73/25.01; 422/68.1; 422/78; 585/833; 585/801
[58] Field of Search .............. 73/23.41, 25.01, 23.35; 95/167, 143, 205, 102, 93; 585/833, 801; 422/68.1, 69, 78

[56] References Cited

U.S. PATENT DOCUMENTS

| | | | |
|---|---|---|---|
| 2,492,401 | 12/1949 | Schutte | 95/93 |
| 3,346,341 | 10/1967 | Sternberg | 73/23.35 |
| 3,847,546 | 11/1974 | Paul | 73/23.35 |
| 4,244,917 | 1/1981 | Woods et al. | 422/78 |
| 4,305,734 | 12/1981 | McGill | 55/25 |
| 4,384,471 | 5/1983 | Wentzel | 73/23.1 |
| 4,509,855 | 4/1985 | Gay | 356/72 |
| 4,919,893 | 4/1990 | Bandurski et al. | 422/78 |
| 5,191,211 | 3/1993 | Gorman, Jr. | 250/282 |
| 5,242,245 | 9/1993 | Schellstede | 405/128 |

FOREIGN PATENT DOCUMENTS

| | | | |
|---|---|---|---|
| 0235480 | 9/1987 | European Pat. Off. | |
| 2192657 | 8/1987 | Japan | 73/23.35 |
| 2201156 | 8/1990 | Japan | 73/23.35 |
| 2203268 | 8/1990 | Japan | 73/23.35 |
| 2161269 | 1/1986 | United Kingdom | |
| 1404933 | 6/1988 | U.S.S.R. | 73/23.35 |

*Primary Examiner*—Thomas P. Noland
*Assistant Examiner*—J. David Wiggins
*Attorney, Agent, or Firm*—Oblon, Spivak, McClelland, Maier & Neustadt

[57] ABSTRACT

A method for separating and analyzing the hydrocarbons, particularly heavy hydrocarbons, contained in sedimentary rocks, comprising:
A) loading a sample tube with the sample of sedimentary rock and one or more inert solvents;
B) preheating the sample tube;
C) removing the solvent and the hydrocarbons previously contained in the rock;
D) condensing the vapour and feeding it to a separation and analysis device.

The invention also comprises an apparatus for implementing separating and analyzing method.

15 Claims, 4 Drawing Sheets

METHOD FOR DETERMINING HEAVY HYDROCARBONS IN ROCK MATRICES AND THE APPARATUS FOR THE PURPOSE

This invention relates to a method for determining heavy hydrocarbons contained in rock matrices.

The invention also relates to an apparatus for effecting said determination.

The term "heavy hydrocarbons" is intended to mean hydrocarbons containing 15 or more carbon atoms.

Analysis of the biological markers present in sedimentary rocks or in fossil materials is a problem of fundamental importance in organic geochemistry.

A generally used method for analyzing said rocks comprises firstly extracting the rock with a suitable solvent, then analyzing the extracts by GC-FID or GC-MS. This method is however costly because it requires a rather lengthy time for extracting the rock matrix and also because sometimes the extracts cannot be immediately used for gas-chromatography analysis because further preparative chromatography separation steps are required.

An alternative method is based on thermal desorption (TD), consisting of vaporizing (by heating to a temperature of about 320° C.) the compounds contained in the rock and then directly analyzing them by GC.

This method operates in the following manner:

- a sample of sedimentary rock in powder form is placed in a sample tube closed at one end by an inert material, preferably glass wool, and the sample tube filled in this manner is placed in a seat through which an inert gas stream passes;
- using a suitable program, the temperature of the sample tube is raised to the desired value, usually about 320° C.;
- the gas stream conveys the hydrocarbons desorbed from the rock to a cryogenic trap, the purpose of which is to condense said hydrocarbons;
- the gas flow to the sample tube is interrupted and the cryogenic trap containing the condensates is heated; gas-chromatography analysis by temperature gradient is simultaneously commenced; the inert gas stream, its passage through the sample tube being interrupted, now passes through the heated trap and transfers the hydrocarbons to the gas-chromatography column, which is provided with a splitter to enable the required gas quantity to be fed through.

This method has the drawback that the heavy hydrocarbons are often retained in the rock matrix, so falsifying the result of the analyses, which are aimed mainly at ascertaining the type and quantity of heavy hydrocarbons present in the matrix.

A method obviating the aforesaid drawbacks has now been found for analyzing the hydrocarbons contained in sedimentary rocks, which represents a modification to the thermal desorption analysis method.

In accordance therewith, the present invention provides a method for separating and analyzing the hydrocarbons, particularly heavy hydrocarbons, contained in sedimentary rocks, characterised by comprising the following steps:

A) loading a sample tube with a sample of sedimentary rock and one or more inert solvents;
B) preheating the thus loaded sample tube to a temperature of between 60° and 150° C. and maintaining it at this temperature in an inert gas atmosphere;
C) heating the sample tube in an inert gas stream to a temperature such as to remove the solvent and the hydrocarbons previously contained in the rock;
D) condensing the vapour conveyed by the inert gas in a refrigerated container;
E) heating said container and feeding the contents by means of said inert transport gas to a separation and analysis means.

The invention is further clarified hereinafter with reference to the accompanying figures.

FIG. 1 shows various chromatograms resulting from treating the rock sample with dichloromethane for 30 seconds (chromatogram a), 2 minutes (chromatogram b) and 3 minutes (chromatogram c). The horizontal axis represents the time in minutes and the vertical axis the peak intensity. The chromatograms also indicate the number of carbon atoms of some significant peaks.

In order not to interfere with the subsequent gas-chromatography analyses, the inert solvent is preferably chosen from hydrocarbons or chlorinated hydrocarbons with a boiling point at atmospheric pressure lower than about 100° C. A mixture of such solvents can also be used. For example n-pentane, n-hexane, heptane or methylene chloride can be used for the purpose. The preferred solvent quantity depends on various parameters, in particular the quantity of rock matrix to be analyzed. Usually for a rock matrix quantity of between 1 and 10 mg it is preferable to use between 5 and 50 microliters of solvent.

The sample tube is constructed of thermally stable, preferably inorganic inert material, such as glass or quartz.

To achieve more intimate contact between the solvent and the rock matrix, the rock matrix is preferably in powdered form, with an inert containing means, preferably glass wool, present for said powder.

In addition, the sample tube is preferably occupied by the sample only at one end, the other end remaining free.

In step (B), in order to extract practically all the hydrocarbons from the rock, the temperature is raised to between 60° and 150° C., and preferably between 80° and 110° C.

During this step it is preferable to effect the preheating by heating only that end of the sample tube carrying the sample; this allows the released hydrocarbons to recondense along the entire tube.

Figure 1C:
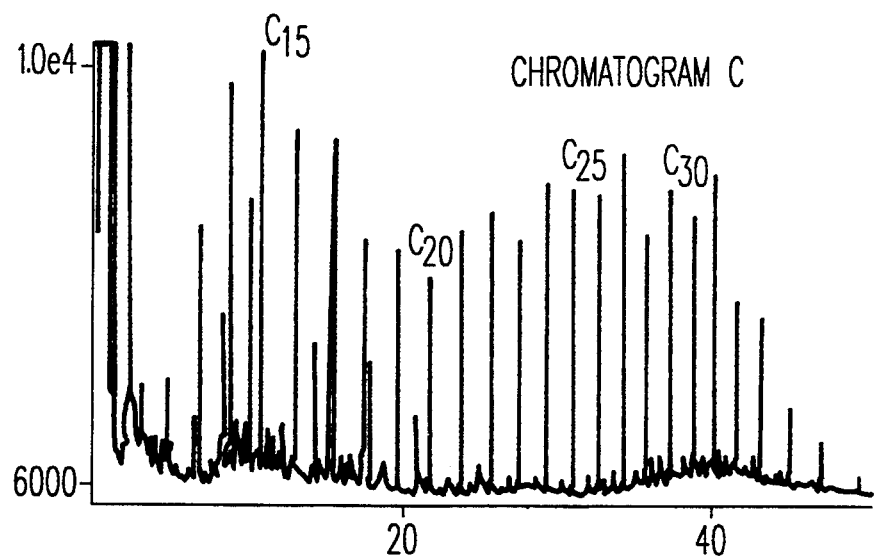
Figure 1B:
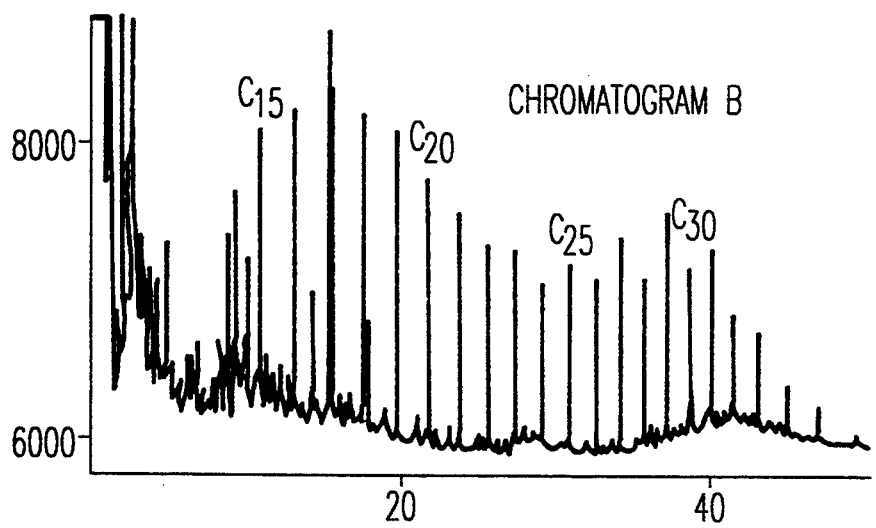
Figure 1A:
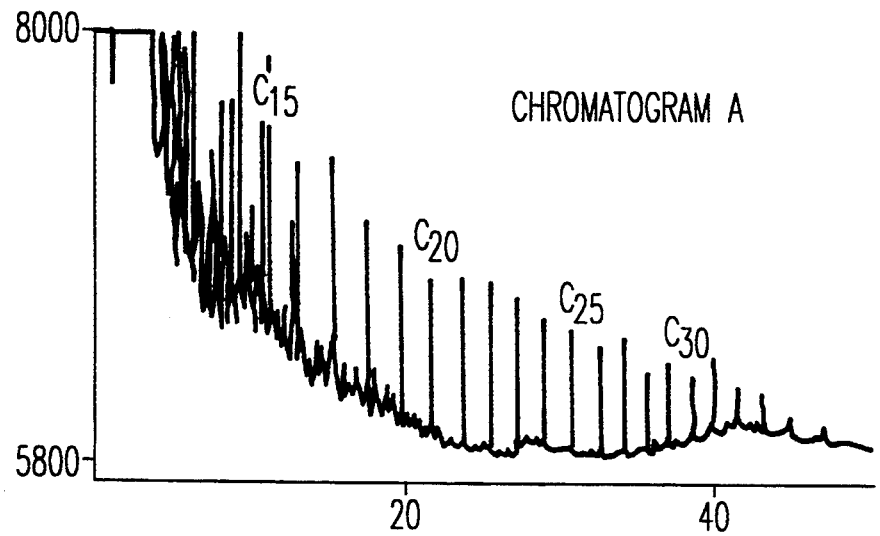

The time for which the rock material and the solvent are maintained at the aforesaid temperature is critical. In this respect the solvent must remain in contact with the sample of rock matrix for a time sufficient to achieve virtually total extraction of the hydrocarbons contained in the rock. FIG. 1 shows the various chromatograms resulting from treating an identical sample of rock matrix with dichloromethane at about 95° C. for a time of 30 seconds, 2 minutes and 3 minutes respectively. After 3 minutes the chromatograms are virtually identical.

Hence under these conditions the contact time between the rock and solvent must be at least 3 minutes.

Figure 2A:
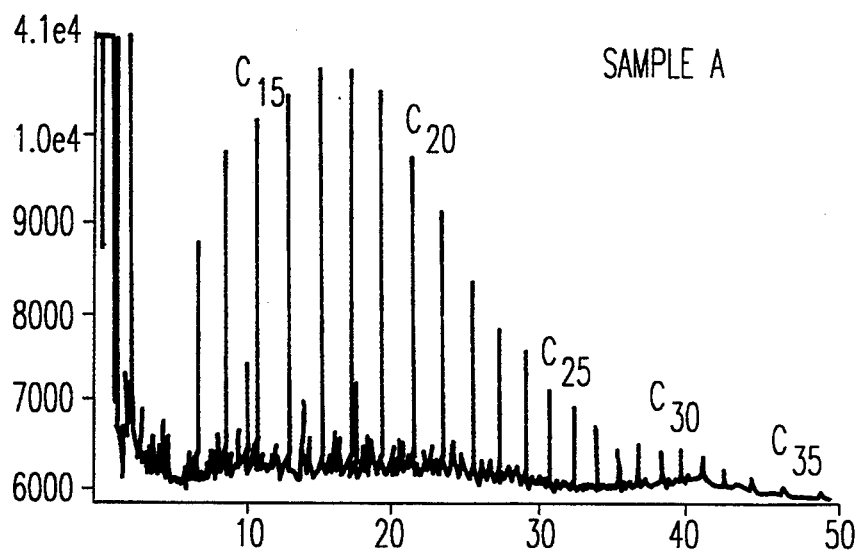
FIG. 2 shows the chromatograms deriving from three different rock matrices (samples A, B and C) subjected to the method of the present invention.
Figure 2B:
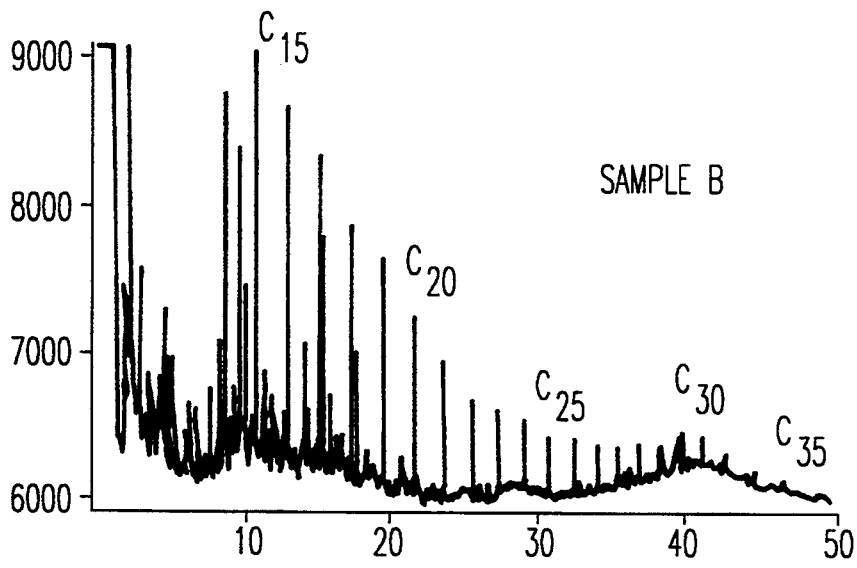
Figure 2C:
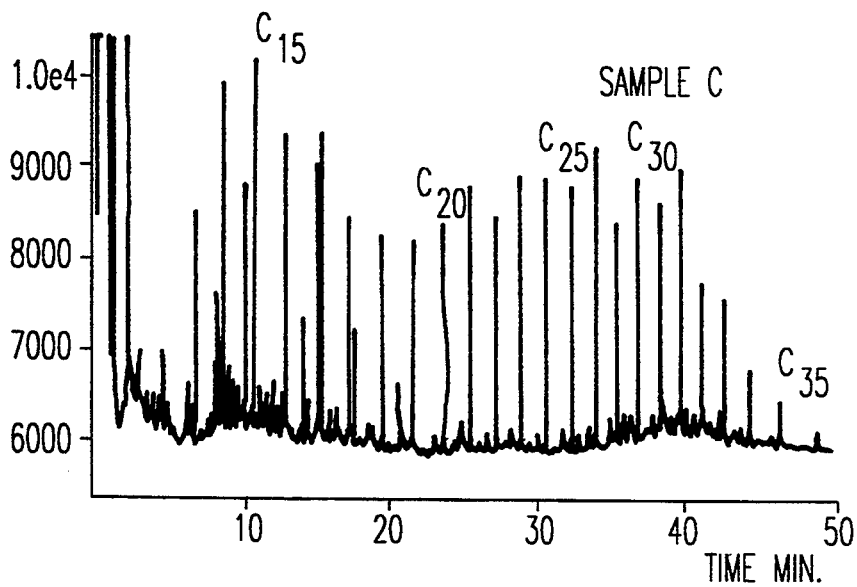
Figure 3A:
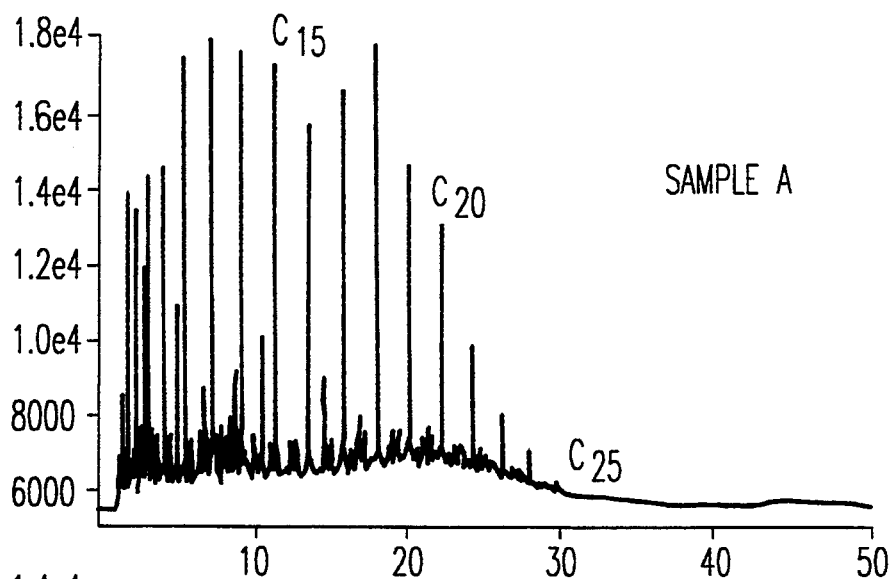
FIG. 3 shows the chromatograms deriving from the rock matrices of FIG. 2, but subjected to usual thermal desorption.
Figure 3B:
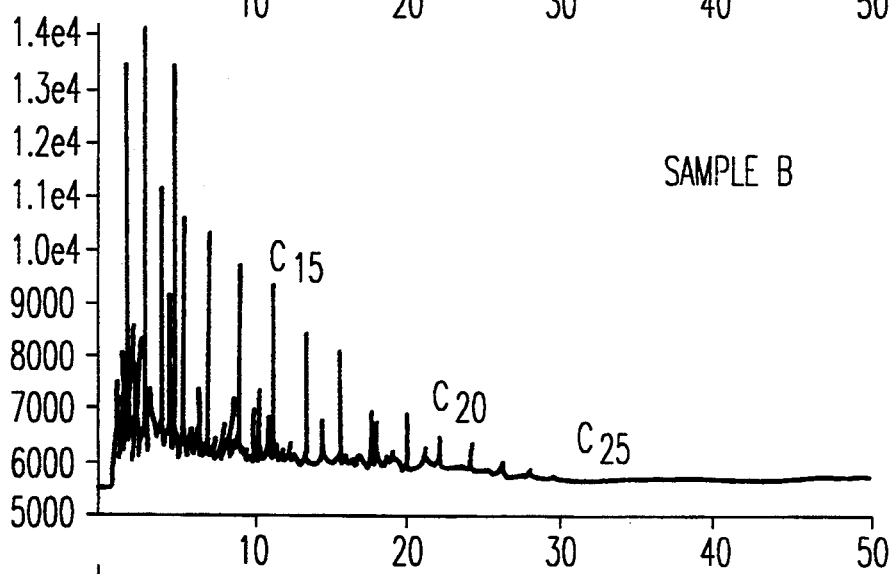
Figure 3C:
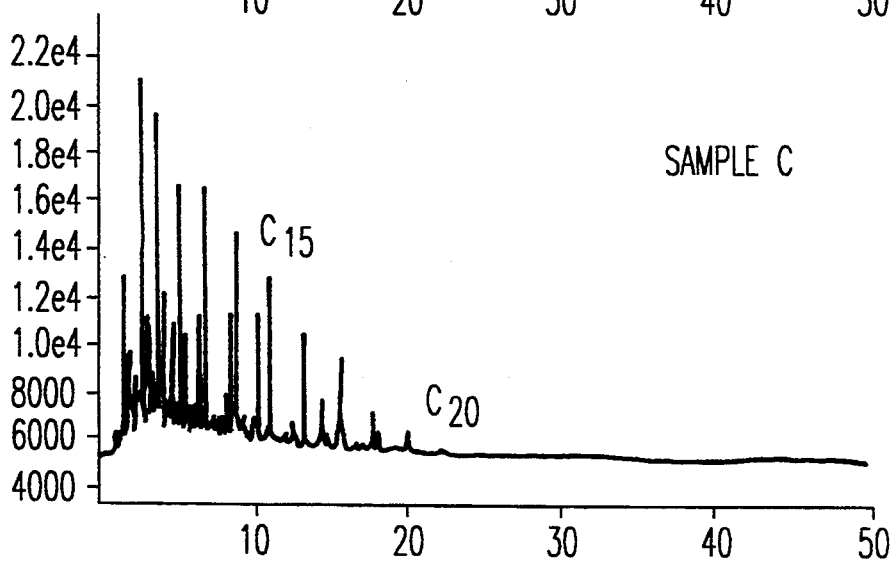

The advantage of operating by the method of the present invention is apparent from FIGS. 2 and 3. FIG. 2 shows the chromatograms deriving from three different rock matrices subjected to the method of the present invention, while FIG. 3 shows the chromatograms deriving from the same rock matrices subjected to usual thermal desorption. It is immediately apparent that only by the method of the present invention can certain hydrocarbons be determined which would not be determinable by the usual thermal desorption method.

On termination of step (B), the sample tube is heated in an inert gas stream (step C) to a temperature such as to ensure complete removal of the extracted hydrocarbons. With a gas flow preferably of between 20 and 60 ml/min, the sample tube should be heated to a temperature of between 220° and 340° C., preferably between 240° and 320° C., and even more preferably to a temperature of about 300° C. The hydrocarbons from the rock are then condensed (step D) in a means, preferably a trap, cooled to a temperature which ensures complete condensation of the hydrocarbons. In the preferred embodiment of the present invention, the trap is cooled to a temperature of between −100° and −20° C., and preferably to about −30° C. In this manner all the heavy hydrocarbons previously contained in the rock matrix are condensed. If the lighter hydrocarbon part is also to be analyzed, cooling can take place to a temperature of down to −150° C. At this temperature all the light hydrocarbons are condensed, but their analysis, of lesser interest in terms of the information obtainable, is disturbed by the presence of the solvent used in step (A).

The trap must be constructed of an inert material resistant to thermal stress and such as not to emit substances able to contaminate the composition to be analyzed.

When the hydrocarbons have condensed in the trap, they are fed to the gas chromatograph in an inert gas-stream. This feed is achieved by heating (step E) the previously cooled trap to a temperature of between 220° and 340° C. and preferably to about 300° C.

The hydrocarbon separation and analysis means is a usual gas chromatograph, possibly coupled to a mass spectrometer.

The present invention further provides an apparatus for analyzing the hydrocarbons, particularly heavy hydrocarbons, contained in rock matrices, comprising, possibly in cooperation with a movable heater, a sample tube of inert material through which an inert transport gas is conveyed via a pipe provided with a pressure regulator and indicator and a solenoid valve, and which has its exit connected to a multi-way valve connected via an interface to a trap able to condense the vapours originating from the sample to be analyzed and from the solvent used and then, when required, to release them by heating them in an inert gas stream; said trap being connected to a separation and analysis system, characterised in that a non-return element for the gas and a heating element are inserted between said solenoid valve and said sample tube respectively.

In the preferred embodiment, said non-return element consists of a non-return valve or a capillary restriction, and the heating element consists of a resistance element.

Figure 4:
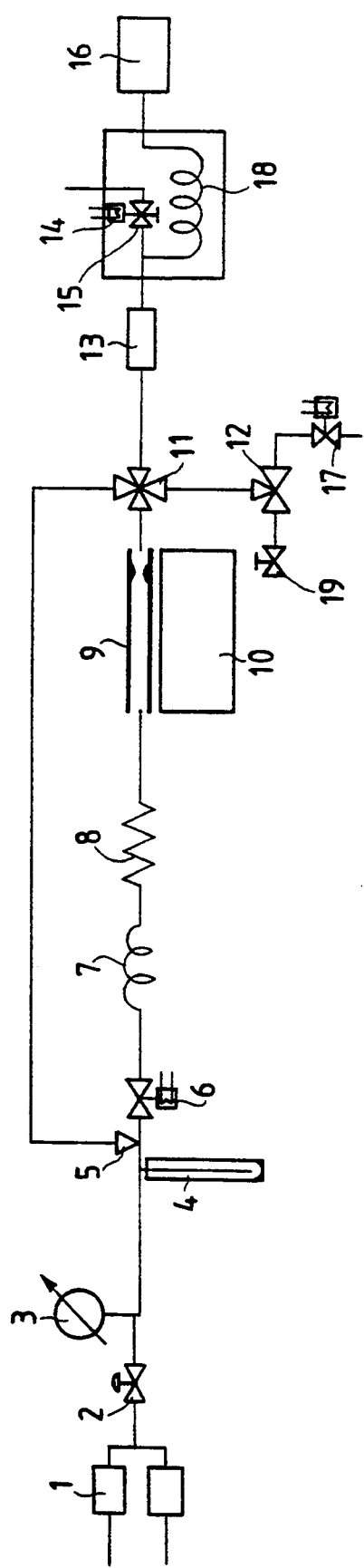
FIG. 4 is a scheme of an apparatus usable for implementing the method of the present invention.

Optionally, said apparatus can be provided with a system for cleaning the lines of any hydrocarbon impurities which accumulate, said system consisting of a small vessel (not shown in the Figures) containing a solvent chosen from those used in the extraction, into which a wick dips. FIG. 4 shows the preferred embodiment of the apparatus of the present invention, by way of non-limiting illustration.

In FIG. 4, the reference numeral 1 indicates two alternately operating solenoid shut-off valves; 2 is a pressure regulator; 3 is a pressure indicator; 4 is the optional line cleaning device; 5 is a by-pass line; 6 is a solenoid valve; 7 is a capillary functioning as the non-return element, which can alternatively be a non-return valve; 8 is a line portion heated by a resistance element to about 150° C., however as an alternative the heating system can consist of a refractory paste with an embedded resistor and/or a thermocouple for temperature control; 9 is the sample tube; 10 is a movable heater consisting of a suitably shaped aluminium block maintained constantly at the working temperature; 11 is a multi-way valve; 12 is a 3-way valve; 13 is the cooled trap able to operate between −150° and +340° C.; 14 is the gas chromatograph heater; 15 is a splitter valve; 16 is a usual gas chromatograph detector of conductivity or flame ionization type; 17 is a splitter valve; 18 is the gas chromatography column; 19 is au adjustable vent valve.

With reference to FIG. 4, the apparatus of the present invention operates in the following manner.

The transport gas is either hydrogen or helium, depending on the gas chromatograph detector. In the case of hydrogen the inlet pressure is about 0.5 kg/cm$^2$, whereas with helium the pressure is between 0.7 and 0.8 kg/cm$^2$. The gas passes through the shut-off valve 1 and is then regulated by the pressure regulator 2 to the required pressure which is read on the pressure indicator 3. Optionally, the gas can pass through the device 4 containing a solvent, generally that used for extracting the hydrocarbons from the rock matrix, so that it entrains part of the solvent in order to clean the lines of any hydrocarbon traces from the previous analyses. After passing the point 4 the transport gas is split into two branches.

By virtue of the multi-way valve 11 the line 5 enables the extracted and thermally desorbed hydrocarbons to be transferred from the trap 13 to the gas chromatography column.

The other branch comprises the solenoid valve 6 which is closed during replacement of the sample tube, the restriction 7, the temperature-controlled line 8, the sample tube 9 and the heater 10.

The rock sample to be examined is suitably ground and placed in the sample tube together with a few microliters of solvent. The multi-way valve 11 is constantly heated to about 300° C. by a temperature-controlled metal block 10 to prevent hydrocarbon recondensation during transfer. Because of the closeness of the valve 11 to the sample tube 9, that end of the sample tube containing the sample to be analyzed and the solvent is heated to about 95° C. The time for which the sample tube 9 is heated at the sample end is at least 3 minutes. During this step, the hydrocarbons extracted from the rock condense at the opposite cold end of the sample tube 9, during which the gas present in the sample tube 9 is blocked by the valve 11, hence enabling the transfer gas of the line 5 to pass downstream.

After this hot contact between the solvent and the rock matrix to be examined, the heater 10, already at about 300° C., descends onto the tube and the valve 11 is simultaneously switched over.

The transport gas from the line 5 is hence intercepted to enable the thermally desorbed extract from the sample tube to be transferred to the trap 13. During this step the three-way valve 12 is connected to the closed solenoid valve 17. The vapour arising from the few microliters of solvent cannot be instantaneously transferred to the cooled trap and tends to diffuse rearwards towards the feed line. The capillary restriction 7 and the heated line portion 8 prevent this vapour retrodiffusion and condensation phenomenon, so allowing the vapour to flow out as required.

The time usually required for condensing the vapour in the trap is about 15 minutes.

As the trap is cooled to about −30° C. and the dichloromethane solvent is very volatile, the solvent and the light hydrocarbons are not completely retained, whereas the heavy hydrocarbons are completely retained in the trap.

Anything not retained in the trap is transported by the inert gas into the gas chromatography heater 14 where it encounters a branch to which there are connected an adjustable splitter 15, this being open during this step to allow the light products to be discharged to the outside, and a gas chromatography column 18 connected to a detector 16.

Depending on the pressure drop ratio between the column and the splitter, the transport gas also partly enters the gas chromatography column 18. As the column heater is at about 50° C., the dichloromethane present in the transport gas is urged to the outlet where the detector detects its presence. Following the entire step by a potentiometer connected to the detector, the trace obtained represents an enormous solvent peak which dies off in time.

After the extraction and desorption step, the trap is rapidly heated to about 300° C., and the splitter is closed to compel the released hydrocarbons to enter only the column 18, where a suitable temperature program (for example 50° C. for two minutes, then to 100° C. after a further two minutes and 300° C. after 40 minutes, to remain at 300° C. for 20 minutes and return to 50° C. within 10 minutes) allows gas chromatography analysis possibly combined with mass spectrometry.

After the programmed temperature phase, the splitter 15 is again opened to restore the initial configuration.

During the gas chromatography analysis, and without altering the setting of the valve 11, a new sample tube 9 containing only glass wool can be placed in its seat. By operating the three-way valve 12, the tube can be connected to the valve 19. As the heater 10 can be moved manually, it can be lowered onto the sample tube and the inert gas stream used to eliminate contaminants contained in the glass wool through the valve 19. The decontamination operation is hence achieved in an analytically correct manner and has the advantage of being effected without interruption of any operating step.

When this has been done, the operator sets the valve 12 to its initial position so that the system is ready for a new analysis.

I claim the following:

1. A method for separating and analyzing the hydrocarbons, particularly heavy hydrocarbons, contained in sedimentary rocks, characterised by comprising the following steps:

A) loading a sample tube with the sample of sedimentary rock and one or more inert solvents able to extract the hydrocarbons contained in the rock;
B) preheating the thus loaded sample tube to a temperature of between 60° and 150° C. and maintaining it at this temperature in an inert gas atmosphere;
C) heating the sample tube in an inert gas stream to a temperature such as to remove the solvent and the hydrocarbons previously contained in the rock;
D) condensing the vapour conveyed by the inert gas in a refrigerated container;
E) heating said container and feeding the contents by means of said inert transport gas to a separation and analysis means.

2. A method as claimed in claim 1, characterised in that the inert solvent is chosen from hydrocarbons or chlorinated hydrocarbons with a boiling point at atmospheric pressure lower than about 100° C.

3. A method as claimed in claim 2, characterised in that the inert solvent is dichloromethane.

4. A method as claimed in claim 1, characterised in that the contact time (step B) between the solvent and the rock matrix is at least three minutes.

5. A method as claimed in claim 1, characterised in that step B is effected at a temperature of between 80° and 110° C.

6. A method as claimed in claim 1, characterised in that in step C the sample tube is heated to a temperature of between 220° and 340° C.

7. A method as claimed in claim 6, characterised in that the temperature is between 240° and 320° C.

8. A method as claimed in claim 7, characterised in that the temperature is about 300° C.

9. A method as claimed in claim 1, characterised in that in step D the vapours are condensed in a means refrigerated to a temperature of between −100° and −30° C.

10. A method as claimed in claim 1, characterised in that in step E the previously cooled container is heated to a temperature of between 220° and 340° C.

11. An apparatus for analyzing the hydrocarbons, particularly heavy hydrocarbons, contained in rock matrices, comprising, in cooperation with a movable heater, a sample tube of inert material through which an inert transport gas is conveyed via a pipe provided with a pressure regulator and indicator and a solenoid valve, and which sample tube has its exit connected to a multi-way valve connected via an interface to a trap able to condense the vapours originating from the sample to be analyzed and from the solvent used, and then, when required, to release the condensed vapors by heating them in an inert gas stream; said trap being connected to a separation and analysis system, characterised in that a non-return element for the gas and a heating element are inserted between said solenoid valve and said sample tube respectively.

12. An apparatus as claimed in claim 11, characterised in that the non-return element is a non-return valve.

13. An apparatus as claimed in claim 11, characterised in that the non-return element is a capillary restriction.

14. An apparatus as claimed in claim 11, characterised in that the heating element is a resistance element.

15. An apparatus as claimed in claim 11, characterised in that a vessel (for self-cleaning apparatus) containing solvent into which a wick dips is inserted between the pressure indicator and regulator and the multi-way valve.

* * * * *